US 008124714B2

(12) United States Patent
Bissinger et al.

(10) Patent No.: US 8,124,714 B2
(45) Date of Patent: Feb. 28, 2012

(54) SILICON-UREA-AZOLIDES, THEIR PREPARATION AND USE IN THE PREPARATION OF SILICONES WITH ISOCYANATE TERMINAL GROUPS

(75) Inventors: Peter Bissinger, Diessen (DE); Wolf Steiger, Geretsried (DE)

(73) Assignee: 3M Innovative Properties Company, Saint Paul, MN (US)

( * ) Notice: Subject to any disclaimer, the term of this patent is extended or adjusted under 35 U.S.C. 154(b) by 585 days.

(21) Appl. No.: 12/091,552

(22) PCT Filed: Oct. 27, 2006

(86) PCT No.: PCT/US2006/042105
§ 371 (c)(1),
(2), (4) Date: Apr. 25, 2008

(87) PCT Pub. No.: WO2007/050950
PCT Pub. Date: May 3, 2007

(65) Prior Publication Data
US 2009/0258999 A1   Oct. 15, 2009

(30) Foreign Application Priority Data

Oct. 27, 2005  (EP) .................................. 05023543

(51) Int. Cl.
*C08G 77/26* (2006.01)
(52) U.S. Cl. ........................................................ 528/27
(58) Field of Classification Search .................... 528/27
See application file for complete search history.

(56) References Cited

U.S. PATENT DOCUMENTS

| | | | |
|---|---|---|---|
| 3,170,891 A | 2/1965 | Speier | |
| 3,179,622 A | 4/1965 | Haluska | |
| 3,179,633 A | 4/1965 | Endrey | |
| 3,607,901 A | 9/1971 | Berger | |
| 3,936,484 A | 2/1976 | Rosenthal et al. | |
| 4,518,758 A | 5/1985 | Cavezzan et al. | |
| 5,157,095 A | 10/1992 | Smid | |
| 5,886,205 A | 3/1999 | Uchida et al. | |
| 2003/0032726 A1 | 2/2003 | Shores | |
| 2006/0207930 A1* | 9/2006 | Yeager et al. | ................ 210/490 |

FOREIGN PATENT DOCUMENTS

| | | |
|---|---|---|
| DE | 42 08 40 2 A1 | 9/1993 |
| EP | 1 496 079 | 1/2005 |
| GB | 1 392 849 | 4/1975 |
| JP | 60-140342 | 7/1985 |
| JP | 60-140343 | 7/1985 |
| JP | 05-008713 | 1/1993 |
| JP | 2001-48855 | 2/2001 |
| WO | WO 91/18006 | 11/1991 |
| WO | WO 93/19366 | 9/1993 |
| WO | WO 02/077072 | 10/2002 |

OTHER PUBLICATIONS

Mark, et al., "Encyclopedia of Polymer Science and Engineering" 2nd Edition, vol. 15, p. 204, (1989) John Wiley & Sons, ISBN 0-471-80947-0.
Ulrich, "Chemistry and Technology of Isocyanates", Wiley (1996).
Costa, et al., "Hybrids of macrolides and necleobases or nucleosides", *Tetrahedron Letters*, vol. 41, No. 18, (Apr. 2000) pp. 3371-3375 (XP004198041).
Glockner, et al., "Synthesis and rheological behavior of cross-linkable poly[N-(methacryl-2-ethyl)-N '-(3-amino(1,2,4-triazole-2-yl))urea-co methyl methacrylate]", *Macromolecules*, vol. 35, No. 6, (Mar. 2002), pp. 2050-2054 (XP002382484).
Gol'din, et al., "Synthesis of organosilicon and organic poly(carbamidotriazoles)", (XP002382575) retrieved from STN Database accession No. 83:79677 in the application abstract Vysokomelekulyarnye Soedineniya, Seriya B: Kratkie Soobshcheniya, vol. 17, No. 4, (1975) pp. 322-323 SP(009066430).
Ivanov, et al., "The effect of solvents on the kinetics of transamination of N-aryl-3-methylpyrazole-1-carboxamides", *Journal of Organic Chemistry of the USSR*, vol. 28, No. 3.2, (1992) pp. 456-460 (XP009066797).
Martin, et al., "Acylierung von Heterocyclen mit Kohlensaurderivation. VII. Synthesen von Bensimidazolo[2,1-b](1,3,5)thiadiazinen", *Journal for Praktische Chemie*, vol. 326, No. 1 (1984), pp. 159-164 (XP009066799).
Otting, et al., "Reaktionsfahige heterocyclische Amide der Kohlensaure, IV.IR-Spektroskopische Untersuchung der Dissoziotion heterocyclischer N-carbonsaureanilide" *Liebigs Annalen Der Chemie*, vol. 622, (1959), pp. 23-30 (XP009066873).
Raspoet, et al., "Experimental and Theoretical Evidence for a Concerted Catalysis of Water Clusters in the Hydrolysis of Isocyanates", *Journal of Organic Chemistry*, vol. 63, No. 20, (Oct. 1998) pp. 6867-6877 (XP002382483).
Staab, et al., "Azolides in Organic Synthesis and Biochemistry" Wiley-VCH, Weinheim, Germany, (1988), pp. 172,188, 273-279 (XP009066427) ISBN 3-52729314-0.
Vostokov, et al., "Reaction of isocyanates with prazol-5-ones" *Chemistry of Heterocyclic Compounds*, vol. 26, No. 8, (1990) pp. 884-886 (XP009066433).
Wipf, et al., "Synthesis of chemoreversible prodrugs of ara-C with variable time-release profiles. Biological evaluation of their apoptotic activity", *Bioorganic & Medicinal Chemistry*, vol. 4, No. 10, (Oct. 1996) pp. 1585-1596 (XP009066434).

* cited by examiner

*Primary Examiner* — Kuo-Liang Peng
(74) *Attorney, Agent, or Firm* — Pamela L. Stewart

(57) ABSTRACT

The invention relates to and their preparation and the production of Silicon-Isocyanates from Silicon-Urea-Azolides.

8 Claims, No Drawings

SILICON-UREA-AZOLIDES, THEIR PREPARATION AND USE IN THE PREPARATION OF SILICONES WITH ISOCYANATE TERMINAL GROUPS

CROSS REFERENCE TO RELATED APPLICATIONS

This application is a national stage filing under 35 U.S.C. 371 of PCT/US2006/042105, filed Oct. 27, 2006, which claims priority to European Patent Application No. 05023543.1, filed Oct. 27, 2005, the disclosure of which is incorporated by reference in its entirety herein.

The invention relates to Silicon-Urea-Azolides and their preparation and the production of silicon isocyanates from Silicon-Urea-Azolides.

Silicone-Isocyanates are valuable chemical building blocks combining properties of silicones and reactivity of isocyanates that are widely applicable in chemical industry. As an isocyanate component, they can be used in many reactive formulations, e.g., to form poly-urethanes or polyureas.

The prior art discloses several procedures for the preparation of Silicone-Isocyanates. Most of them, however, exhibit one or more aspects preventing a facile applicability. Although there is a need for Silicone-Isocyanates they are not readily available on the market.

For application of Silicone-Isocyanates as an reactive intermediate an insoluble and cheaper intermediate step like Silicon-Urea-Azolides in the sequence to Silicone-Isocyanates could be useful.

U.S. Pat. No. 3,170,891 describes synthesis of Silicon-Isocyanates by hydrosilation of unsaturated isocyanates to Si—H functional Silicones. The problem with this reaction lies in the fact that both the unsaturated isocyanates needed as an educt as well as the platinum catalyst are very expensive. Moreover, the reaction often is not nearly quantitative, especially with educts of elevated molecular weights. Additionally, there are side reactions and it is difficult to remove unreacted educt and catalyst due to the polymeric character of the product and its sensitivity to nucleophiles.

U.S. Pat. No. 3,179,622 describes Silicone-Isocyanates made by step-growth polymerization of siloxane amines or siloxane carbinols with an excess of organic diisocyanates. Inevitably, minor amounts of the mostly problematic diisocyanates remain in the product which are difficult to remove. The urea- or urethane-groups resulting from the step growth reaction increase the viscosity of the product (by several magnitudes) compared to material of comparable molecular weight without those urea or urethane groups.

U.S. Pat. No. 3,936,484 describes the production of poly-isocyanates from substituted ureas. The described synthetic methods are directed towards the classical organic low molecular weight diisocyanates (mainly TDI) by pyrolysis of N,N'-bis-ureas. The amines released by pyrolysis are not stabilized by mesomeric structures. Starting ureas are thermally stable and decomposition temperatures therefore are drastic (230-350° C.) and the yields are low, which in case of difunctional ureas leads to high fractions of undesired mono isocyanates.

U.S. Pat. No. 5,886,205 describes the synthesis of siloxane isocyanates by decomposition of urethanes that are produced by reaction of diorgano carbonates and siloxane amines. The decomposition temperature is high (in the examples around 250° C.) leading to undesired thermal degradation and discoloration.

JP 2001-48855 describes the synthesis of "relatively high molecular" siloxane isocyanates by converting Siloxane-Amines into aryl urethanes (using diarylcarbonate). Thermal decomposition of the urethanes gives high yield of Silicone-Isocyanates. The reactions disclosed require rather elevated temperatures and are time consuming. Molecular weights are often unsatisfactorily low.

U.S. Pat. No. 5,886,205 discloses that the production of Silicone-Isocyanates via phosgenation fails because the side product cracks siloxane bonds. Whereas in Japanese patent publication No. 5-8713 (1993) it is disclosed to use tertiary amines to remove HCl, the use of phosgene and the corrosivity of chloride containing reaction mixtures at high temperatures or exhaust gases remain problematic.

H. A. Staab "Azolides in organic synthesis and biochemistry", Wiley-VCH, 1998 [ISBN: 3-52729314-0] S.172, 188, 273-279 describes the decomposability of organic molecular Urea-Imidazolides to give isocyanates and imidazol. It is also mentioned that in some cases even at room temperature the substance shows an isocyanate band around 2250 $cm^{-1}$ in the IR spectrum, proving that the equilibrium is at least partly on the isocyanate side. Isocyanates are isolated in some cases by distillation of the isocyanates from the mixture although with moderate to poor yields (83% at most). The comparatively low yields for isocyanates actually do not recommend an application of this reaction to polymeric substances. Since purification by distillation is impossible for polymeric substrates, keeping in mind that 83% yield in mono isocyanates means statistically 69% yield with diisocyanates and even less for higher functional isocyanates.

G. S. Gol'din, V. G. Poddubnyi, A. N. Kol'tsova, Vysokomol. Soedin Ser. B17(4) (1975) 322-3 describe a polymeric silicon urea triazolide, by reacting silicon isocyanate with a bridged Bis-Triazolide. The polymers are described as showing increased solubility in organic solvents and as lowering the softening point of formulations. No thermal reversibility of the reaction is mentioned. No azolides from monomeric azoles are disclosed.

DE 42 08 40 2 A1 describes the production of Silicone-Isocyanates by condensation of an isocyanate functional dichlorosilane with dihydroxy tetramethyldisiloxane. The preparative scope of this reaction is very limited. The process requires two commercially unavailable raw materials and releases HCl with similar detrimental effects as found with phosgenation.

Expired documents JP 60-140342 and JP 60-140343 describe silverhalogenide containing photographic formulations comprising silicones with pendant reactive groups. Among numerous more precisely specified species in the general description azolides are mentioned.

There has thus been a need for a compound which allows for an easy accessibility of Silicone-Isocyanates. There has also been a need for an easy to use process which can supply such a compound in large amounts and high yields with a high degree of isocyanate functionality and a broad variability of molecular weight.

SUMMARY OF THE INVENTION

The invention relates to an azolide according to the general formula I

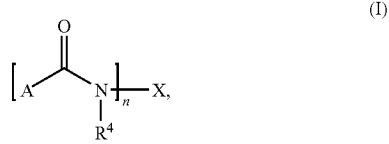

wherein A is an azole ring connected to the carbonyl group via an N atom, $R^4$ is H or a linear or branched or cyclic alkyl group with 1 to 24 C-atoms, X is a monomeric, oligomeric or polymeric radical with the functionality n containing at least one Si atom and n is 1 to about 100000.

The invention further relates to a process for the production of an azolide according to the general formula I

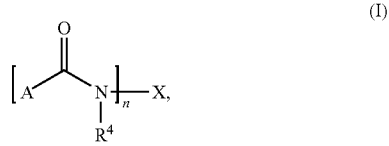

wherein an amino compound according to the general formula $(H_2N—)_nX$, with X being a monomeric, oligomeric or polymeric radical with the functionality n containing at least 1 Si-atom, $R^4$ is H or a linear or branched or cyclic alkyl group with 1 to 24 C-atoms and n is 1 to 100000, is reacted in one or more steps with one or more compounds which form an azolide according to formula I.

The invention also relates to a process for the production of Silicone-Isocyanates wherein an azolide according to the general formula I

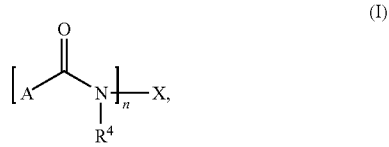

where A is an azole ring connected to the carbonyl group via an N atom, X is a monomeric, oligomeric or polymeric radical with the functionality n containing at least 1 Si-atom, $R^4$ is H or a linear or branched or cyclic alkyl group with 1 to 24 C-atoms and n is 1 to 100000, is decomposed at elevated temperatures.

The Silicon-Urea-Azolides according to the invention are available from the corresponding Silicone-Amines. They can be prepared, e.g., by reaction of the latter with carbonyl bisazolides or by cold phosgenation in the presence of a stoichiometric amount of tertiary base to scavenge HCl and subsequent reaction of the chlorocarbamate with imidazole in the presence of a stoichiometric amount of base to capture HCl.

The described reaction with carbonyl bisazolides in most cases very specifically leads to Silicone-Urea-Azolides with little or no formation of symmetrical urea coming from double reaction with silicone amine. At room temperature within a short time a nearly quantitative reaction of all amino groups present can often be observed. The reaction can be conducted in compatibilizing solvents like THF, non compatibilizing solvents like cyclohexane, mixtures of two or more of these types of solvents or with no solvent at all. Condensation catalysts, though applicable, are not necessarily required.

By heating Silicon-Urea-Azolides under vacuum, the urea groups decompose even at mild conditions reaching equilibrium very fast so that the continuous separation of azole from the vapour phase is possible. The reaction rates are high. Within the contact time of one or several cycles in a thin-film evaporator or short path distiller almost quantitative decomposition and simultaneous removal of the azole can often be achieved. Again, no catalysts are required for the decomposition reaction.

The process for the production of silicon isocyanates according to the invention thus can have one or more of the following advantages:
facile introduction of organic isocyanate function at silicone containing molecules, especially of silicon containing polymers at elevated molecular weights (e.g., above about 500 g/Mole),
no hard to separate metal catalysts
easy to separate by-products,
low cost and commercially available raw material basis,
comparable viscosity of the Silicone-Isocyanates to Silicone-Amines of comparable chain length,
simple processes (if desired: no solvents, no extraction or cleaning procedures),
almost no side reactions,
broad applicability
high degree of functionalization.

The following terms are used in the present text according to the following definitions:

The term "Silicone" refers to the definition given in H. F. Mark et al. "Encyclopedia of Polymer Science and Engeneering" $2^{nd}$ Edition, Volume 15, p 204, (ISBN: 0-471-80947-0 (v. 15)) 1989 John Wiley & Sons, which is expressly mentioned as a valuable source of information on the meaning of the term "silicone" and the disclosure of which is regarded as being part of the disclosure of the present text.

The term "Silicone-Amines" refers to silicones having at least one silicon atom carrying an organic residue comprising a primary amino group ($—NH_2$). The molecule does preferably not comprise other protic or nucleophilic groups (e.g.: OH, COOH, NH, SH), insofar as they are not protected, which are able to react with isocyanate groups.

The term "Silicone-Carbinols" refers to silicones having at least one silicon atom carrying an organic residue comprising an alcohol group (—OH).

The term "Silicone-Isocyanates" refers to silicones having at least one silicon atom carrying an organic residue comprising an isocyanate group (—N=C=O).

The term "Silicon-Urea-Azolides" refers to silicones having at least one silicon atom carrying an organic residue comprising a urea group with a terminal nitrogen which is part of an azole ring as described in the definition for azolides.

The term "Azolide" relates to heterocyclic amides, ureas or urethanes in which the amide nitrogen is part of an azole ring, such as imidazole, pyrazole, triazole, tetrazole, benzimidazole, benzotriazole, and their substituted derivatives", according to H. A. Staab "Azolides in organic synthesis and biochemistry", Wiley-VCH, 1998 [ISBN: 3-527-29314-0].

The term "Carbonyl-Bisazolide" relates to ureas, where both nitrogen atoms are part of an azole ring as described in the definition of azolides.

Azolide-Groups according to the definition of Staab are heterocyclic amides in which the amide nitrogen is part of an azole ring. According to that and the way they are referred to in the cited documents this primarily means azolides of carboxylic acids L not mixed ureas as described in the present text.

The invention will now be explained in further detail.

DETAILED DESCRIPTION OF THE INVENTION

The invention relates to an azolide according to the general formula I

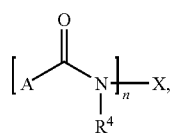

(I)

wherein A is an azole ring connected to the carbonyl group via an N atom, $R^4$ is H or a linear or branched or cyclic alkyl group with 1 to 24 C-atoms, X is a monomeric, oligomeric or polymeric radical with the functionality n containing at least one Si atom and n is 1 to about 100000.

Generally, the invention relates to all types of azolides containing at least one Si atom according to formula I. It is, however, preferred, if the azolide is a molecule with a molecular weight of at least about 250, preferably at least about 350 or at least about 500 or at least about 800 or at least about 1000. Generally, the azolides can be monomeric compounds or oligomeric compounds or polymeric compounds.

X can thus be monomeric, oligomeric or polymeric. In a preferred embodiment, X is an oligomeric or polymeric radical with a molecular weight of at least 200 and at least 2 repetition units with at least 1 Si-atom per repetition unit. X can, e.g., be a linear or branched, saturated or unsaturated or cyclic polysiloxane.

It can be preferred, if Silicone-Urea-Azolides according to formula (I) comprise at least one or more features selected from the following group of features:
a) at least one Si—O—Si bond,
b) one or more groups A-C(=O)N($R^4$)— (as defined in formula (I)) connected to Si atom(s) via an organic spacer,
c) no additional nucleophilic functional groups capable of reacting with isocyanates at room temperature faster than the NH-bond in a urea group (e.g. OH—, NH—, SH—, COOH—),
d) a boiling point at normal pressure (1013 mbar) of >280° C. and/or undergoing decomposition at such a temperature,
e) thermal decomposition at least at one point within a matrix of temperature and pressure defined between 60° C. to 180° C. and $10^{-5}$ mbar to 200 mbar resulting in predominantly Azole and Silicone-Isocyanate and
f) a Molecular weight of more than 230 g/mole.

It can further be preferred if the Silicone-Urea-Azolide comprises a structure $R^1{}_2R^2SiO_{1/2}$ and/or a structure $R^1R^2SiO_{2/2}$ and/or a structure $R^2SiO_{3/2}$ where $R^1$ independently is H, or a linear, branched, cyclic or aromatic saturated or unsaturated facultatively partly or fully fluorinated organic residue with 1 to 30 C-atoms that may contain 0 to 5 O atoms; $R^2$ independently is $R^3$—NH—C(=O)-A; $R^3$ is a bifunctional organic radical alkylen, arylen or mixed with 1 to 18 carbon atoms that may contain 0 to 5 O atoms and A is an azole ring.

It can further be preferred if the Silicone-Urea-Azolide comprises one or more of the following silicone structures:
a) Linear or branched $(R^1{}_2R^2SiO_{1/2})_2(R^1R^2SiO_{2/2})_x$ where $R^1$ independently is H, or a linear, branched, cyclic or aromatic saturated or unsaturated facultatively partly or fully fluorinated organic residue with 1 to 30 C-atoms that may contain 0 to 5 O atoms; $R^2$ independently is $R^1$ but at least one $R^2$ group up to all $R^2$ groups is/are $R^3$—NH—C(=O)-A; $R^3$ is a bifunctional organic radical alkylene, arylene or mixed with 1 to 18 carbon atoms that may contain 0 to 5 O atoms; A is an azole ring; the linear chain may be branched by up to 5 moieties of the structure $R^2SiO_{22}$ and/or $SiO_{4/2}$; x=0 to 100000;
b) cyclic $(R^1R^2SiO_{2/2})_m$ where $R^1$ independently is H, or a linear, branched, cyclic or aromatic saturated or unsaturated facultatively partly or fully fluorinated organic residue with 1 to 30 C-atoms that may contain 0 to 5 O atoms; $R^2$ independently is $R^1$ but at least one $R^2$ group up to all $R^2$ groups is/are $R^3$—NH—C(=O)-A; $R^3$ is a bifunctional organic radical alkylene, arylene or mixed with 1 to 18 carbon atoms that may contain 0 to 5 O atoms; A is an azole ring; m=3 to 1000;
c) polycyclic $(R^2SiO_{3/2})_o$, or $(R^1{}_2R^2SiO_{1/2})_p(SiO_{4/2})_q$ where $R^1$ independently is H, or a linear, branched, cyclic or aromatic saturated or unsaturated facultatively partly or fully fluorinated organic residue with 1 to 30 C-atoms that may contain 0 to 5 O atoms; $R^2$ independently is $R^1$ but at least one $R^2$ group up to all $R^1$ groups is/are $R^3$—NH—C(=O)-A; $R^3$ is a bifunctional organic radical alkylene, arylene or mixed with 1 to 18 carbon atoms that may contain 0 to 5 O atoms; A is an azole ring; o is 6 to 100000 p=1 to q and q is 6 to 100000.

Also preferred can be linear and cyclic siloxanes according to the above described structures with $R^1$ being H, methyl, ethyl, vinyl, ethynyl, propyl, iso-propyl, allyl, propenyl, all isomers of butyl, hexyl, octyl, lauryl and octadecyl, cyclohexyl, phenyl, ethylphenyl, trifluormethyl, 3,3,3-trifluoropropyl, methoxy, ethoxy, propoxy, isopropoxy, 2-methoxyethoxy, 2-ethoxy-ethoxy; $R^2$ independently is $R^1$ but at least one $R^2$ group up to all $R^2$ groups is/are $R^3$—NH—C(=O)-A; $R^3$ is methylene, ethylene, propylene, butylenes, hexylene, octylene, decylene, undecylene, phenylene, ethylenephenylene; A is pyrazolyl, imidazolyl, triazolyl, benzimidazolyl, benzotriazolyl, tetrazolyl; x=0 to 10000; m=3 to 100.

Also preferred can be linear and cyclic siloxanes with $R^1$ being H, methyl, ethyl, vinyl, propyl, iso-propyl, allyl, all isomers of butyl, hexyl, octyl, lauryl and octadecyl, cyclohexyl phenyl, ethylphenyl, trifluormethyl, 3,3,3-trifluoropropyl; $R^2$ independently is $R^1$ but at least one $R^2$ group up to all $R^2$ groups is/are $R^3$—NH—C(=O)-A; $R^3$ is methylene, ethylene, propylene, butylenes, hexylene, octylene, decylene, undecylene, phenylene, ethylenephenylene; A is imidazolyl, triazolyl, benzimidazolyl, benzotriazolyl; x=0 to 10000; m=3 to 100.

Generally, the radicals $R^1$ and $R^2$ can be equipped with any type of substituent or substituents provided they do not interfere with any other constituents or substituents of the composition and do not interfere with the urea azolide group. The term "interfere" as used in the context of the present text relates to any influence of such a substituent on at least one of the other substituents or constituents of the composition or the reaction to form an isocyanate, or both, which is detrimental to the properties of either the urea azolide product or an isocyanate formed from the urea azolide. The term "detrimental" as used in the context of the present text relates to a change of properties that negatively affect the usefulness of the precursors or the cured product in their intended use.

In general, polysiloxane polymers do not comprise uniform chain lengths but show a distribution of various chain lengths as represented by the polydispersity index. Depending an the preparation process, the polydispersity index ranges from 1.1 to 20 and preferably from 1.2 to 10.

Suitable silicone backbones for carrying one or more azolide groups are 1,3-bis(methylene)-1,1,3,3-tetramethyl-disiloxane, 1-3-bis-(3-propylene)-1,1,3,3-tetramethyldisiloxane, 1,3,5,7-tetrakis-(methylene)-1,3,5,7-tetramethyl-cyclotetrasiloxane, 1,3,5,7-tetrakis-(3-propylene)-1,3,5,7-tetramethyl-cyclotetrasiloxane, 1,3,5,7,9-pentakis-(methylene)-1,3,5,7,9-pentamethyl-cyclopentasiloxane, 1,3,5,7,9-pentakis-(3-propylene)-1,3,5,7,9-pentamethyl-cyclopentasiloxane, 1,3,5,7,9,11-hexakis-(methylene)-1,3,5,7,9,11-hexamethyl-cyclohexasiloxane, 1,3,5,7,9,11-hexakis-(3-propylene)-1,3,5,7,9,11-hexamethyl-cyclohexasiloxan, α,ω-alkylene-terminated silicones like α,ω-(methylene)-polydimethylsiloxan, α,ω-(3-propylene)-polydimethylsiloxan and α-alkylene-, ω-trimethylsiloxy terminated silicones like α-methylene-ω-trimethylsiloxypolydimethylsiloxane, α-ethylene-ω-trimethylsiloxypolydimethylsiloxane or α-propylene-ω-trimethylsiloxypolydimethylsiloxane and the like, copolymers of unreactive silicones with alkylene-alkyl-silicones like (3-propylene-methylsiloxan)-co-(dimethylsiloxan) or 1-methylene-methylsiloxane-ω-dimethylsiloxane. The alkylene groups of the above described silicone cycles and polymers carry the azolide groups at the respective alkylene moieties.

A Silicon-Urea-Azolide according to the invention carries at least one azolide group. A Silicon-Urea-Azolide according to the invention can carry only one type of azolide. It is, however, also possible, that a Silicon-Urea-Azolide carries two or more different types of azolide groups. Preferred azolide groups have an imidazole, pyrazole, benzimidazole, triazole, tetrazole or benzotriazole ring. It can be preferred, if no dimeric imidazoles or imidazole derivatives are present. The ring can be substituted or unsubstituted, especially substituted with $C_{1-4}$-alkylgroups, phenyl groups or halogen like F, Cl or Br.

If the backbone of a silicon containing polymer carrying azolide groups is linear or branched, the azolide groups can generally be pendant, terminal or both. It can in some instances be preferred, if a linear oligomer or polymer backbone is carrying the azolide groups as terminal groups.

For the preparation of the Silicon-Urea-Azolides, generally all types of reactions are possible which result in the attachment of at least one azolide group to a silicon containing molecule, preferably a silicone.

According to the inventive process, it can be preferred, if an amino compound according to the formula $(H_2N—)_nX$ is reacted with a compound according to the general formula

with A being an azole ring connected to the carbonyl group via an N atom or where the amino compound according to the formula $(H_2N—)_nX$ is reacted in a first step with phosgene, optionally together with a trialkylamine to scavenge HCl, and in a second step with an azole under formation of an azolide according to the general formula I, where X has the meaning as defined in formula I.

In a preferred embodiment X is a polymeric radical with a molecular weight of at least 200 and at least 2 repetition units with at least 1 Si-atom per repetition unit. Generally, the variable X stands for oligomeric and polymeric backbones as described in the context of the present invention.

Preferred amino compounds are Silicone-Amines that comprise at least one or more features selected from the following group of features:

a) at least one Si—O—Si bond, b) one or more groups $HN(R^4)—$ (as defined in formula (I)) connected to Si atom(s) via an organic spacer, c) no additional nucleophilic functional groups capable of reacting with isocyanates at room temperature faster than the NH-bond in a urea group (e.g. OH—, NH—, SH—, COOH—).

It can further be preferred if an amino compound comprises one or more of the following silicone structures:

a) Linear or branched $(R^1{}_2R^5SiO_{1/2})2(R^1R^5SiO_{2/2})_x$ where $R^1$ independently is H, or a linear, branched, cyclic or aromatic saturated or unsaturated facultatively partly or fully fluorinated organic residue with 1 to 30 C-atoms that may contain 0 to 5 O atoms; $R^5$ independently is $R^1$ but at least one $R^5$ group up to all $R^5$ groups is/are $R^3—NH_2$; $R^3$ is a bifunctional organic alkylene, arylene or mixed radical with 1 to 18 carbon atoms that may contain 0 to 5 O atoms; the linear chain may be branched by up to 5 moieties of the structure $R^5SiO_{2/2}$ and/or $SiO_{4/2}$; x=0 to 100000;

b) cyclic $(R^1R^5SiO_{2/2})_m$ where $R^1$ independently is H, or a linear, branched, cyclic or aromatic saturated or unsaturated facultatively partly or fully fluorinated organic residue with 1 to 30 C-atoms that may contain 0 to 5 O atoms; $R^5$ independently is $R^1$ but at least one $R^5$ group up to all $R^2$ groups is/are $R^3—NH_2$; $R^3$ is a bifunctional organic radical alkylene, arylene or mixed with 1 to 18 carbon atoms that may contain 0 to 5 O atoms; m=3 to 1000;

c) polycyclic $(R^5SiO_{3/2})_o$, or $(R^1{}_2R^5SiO_{1/2})_p(SiO_{4/2})_q$ where $R^1$ independently is H, or a linear, branched, cyclic or aromatic saturated or unsaturated facultatively partly or fully fluorinated organic residue with 1 to 30 C-atoms that may contain 0 to 5 O atoms; $R^5$ independently is $R^1$ but at least one $R^5$ group up to all $R^5$ groups is/are $R^3—NH_2$; $R^3$ is a bifunctional organic alkylene, arylene or mixed radical with 1 to 18 carbon atoms that may contain 0 to 5 O atoms, o is 6 to 100000 p=1 to q and q is 6 to 100000.

Suitable amino silicones of the general formula $(H_2N—)_n X$ are 1,3-bis-(aminomethyl)-1,1,3,3-tetramethyl-disiloxane, 1-3-bis-(3-aminopropyl)-1,1,3,3-tetramethyldisiloxane, 1,3,5,7-tetrakis-(aminomethyl)-1,3,5,7-tetramethyl-cyclotetrasiloxane, 1,3,5,7-tetrakis-(3-aminopropyl)-1,3,5,7-tetramethyl-cyclotetrasiloxane, 1,3,5,7,9-pentakis-(aminomethyl)-1,3,5,7,9-pentamethyl-cyclopentasiloxane, 1,3,5,7,9-pentakis-(3-aminopropyl)-1,3,5,7,9-pentamethyl-cyclopentasiloxane, 1,3,5,7,9,11-hexakis-(aminomethyl)-1,3,5,7,9,1-hexamethyl-cyclohexasiloxane, 1,3,5,7,9,11-hexakis-(3-aminopropyl)-1,3,5,7,9,11-hexamethylcyclohexasiloxane, α,ω-alkyl-terminated silicones like α,ω-(aminomethyl)-polydimethylsiloxane, α,ω-(3-aminopropyl)-polydimethylsiloxane, copolymers of unreactive silicones with aminoalkyl-alkyl-silicones like (3-aminopropyl-methylsiloxane)-co-(dimethylsiloxane).

Further preferred structures are for example R$^1$$_3$Si—O—[SiR$^1$$_2$—O—]$_a$SiR$^1$$_2$—Y—(O—R$^2$)$_d$-T$_e$-[(O—R$^2$)$_b$—NHR$^3$]$_c$ or [HR$^3$N—(R$^2$—O)$_b$]$_c$-T$_e$-(R$^2$—O)$_d$—Y—[SiR$^1$$_2$—O—]$_a$SiR$^1$$_2$—Y—(O—R$^2$)$_d$-T$_e$-[(O—R$^2$)$_b$—NHR$^3$]$_c$ or R$^1$$_3$Si—O—{[SiR$^1$$_2$—O—]$_n$[SiR$^4$(—Y—(O—R$^2$)$_d$-T$_e$-[(O—R$^2$)$_b$—NHR$^3$]$_c$)—O—]$_m$}—SiR$^1$$_3$ or

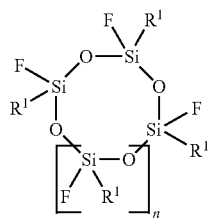

wherein T is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, R$^1$ is a linear or branched alkyl or fluoroalkyl group with 1 to 8 C-atoms or a cycloalkyl or aryl group with 6 to 14 C-atoms, R$^1$ is a linear or branched allylene group that may contain a carbonyl group with 1 to 8 C-atoms, F is R$^1$ or —Y—(O—R$^2$)$_d$-T$_e$-[(O—R$^2$)$_b$—NHR$^3$]$_c$ with at least one residue —Y—(O—R$^2$)$_d$-T$_e$-[(O—R$^2$)$_b$—NHR$^3$]$_c$ per molecule, R$^3$ is a linear or branched alkyl or fluoroalkyl group with 1 to 8 C-atoms or a cycloalkyl or aryl group with 6 to 14 C-atoms or HR$^4$ is R$^1$ or Methoxy or Ethoxy, 1≤a≤10.000, 0≤b≤500, 1≤c≤6, 0≤d≤500, e is 0 or 1, 0≤n≤500, 0≤m≤100 where m+n exceed 5 and x is 0, 1, 2, 3, 4, 5 or 6.

Also suitable and often preferred are:

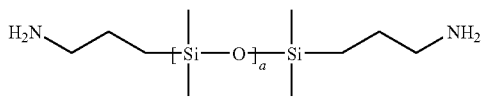

like PDMS Diamine 5 k, 10 k or 15 k from 3M or Tegomer A-Si 2120 or 2130 from Th. Goldschmidt or DMS-A11, A12, A15, A25 or A32 from Gelest (CAS: 106214-84-0)

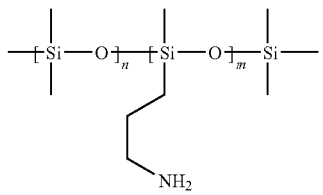

like Rhodorsil 21643 and 21644 from Rhône-Poulenc or AMS-132, 152, and 162 from Gelest (CAS: 99363-37-8) or

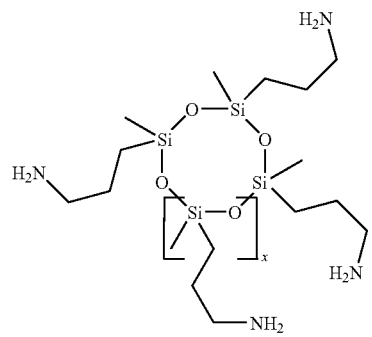

with x=0 to 20, synthesized from Si—H cycles by hydrosilylation with acrylonitrile and subsequent reaction with LiAlH$_4$.

Also preferred can be an amino functionalized polydialkyl disiloxane, especially α,ω-polydimethyldisiloxane (PDMS) with a molecular weight of between about 800 and about 50000, especially between about 100 and about 20000, e.g., between about 2000 and about 10000.

In a further embodiment, silicone amines are reacted with carbonyl-bisazolides in a ratio of at least 1 mol carbonyl bisazolide per 1 equivalent of silicone amine. In some cases an excess of carbonyl bisazolid can be advantageous in order to avoid chain extension. The process, however, under appropriate conditions gives good results even with a very low excess.

For some applications chain extension is desirable as described in U.S. Pat. No. 3,179,633 or WO 02/077072 or EP 1 496 079. By variation of the ratio of carbonyl-bisazolide per equivalent of Silicone-Amine from 1:1 towards 1:2 chain extended, urea segmented terminal Silicone-Urea-Azolides can easily and conveniently be prepared. There chain extended urea segmented terminal Silicone-Urea-Azolides decompose thermally selectively at the terminal Urea-Azolide group resulting in chain extended urea segmented terminal Silicone-Isocyanates.

Generally all types of bisazolides can be used according to the invention. It is, however, preferred to used carbonyl bisazolides. Preferred substances are 1,1'-carbonyl-diimidazol (CDI) CAS-#: [530-62-1], 1,1'-carbonyl-dibenzimidazol CAS-#: [14667-54-0], 1,1'-carbonyl-di-(1,2,4)-triazol CAS-#: [41864-22-6], 1,1'-carbonyl-bis-(2-methylimidazol) CAS-#: [13551-83-29), 1,1'-carbonyl-dibenzotriazol CAS-#: [68985-05-7]. The compounds can be used alone or as a mixture of two or more of them.

The reaction can be conducted with or without solvents. If a solvent is used, it should be a solvent which is inert with regard to the azolide reaction. In some cases THF as a compatibilizer results in accelerated reaction of the carbonyl bisazolide with the silicone amine. Further suitable solvents are cyclohexane, toluene, chloroform or dichloromethane or mixtures of two or more of those.

The reaction temperature can generally between 0 and about 120° C. It can be preferred, if the reaction is conducted at a temperature of between about 5 and about 100° C. or between about 10 and about 40° C. or up to the boiling point of the solvent at normal pressure, if any solvent is used.

Using temperatures below room temperature (about 23° C.) is possible though generally unnecessary. Elevated temperatures of up to 80° C. can facilitate and accelerate the reaction which can be advantageous especially if the process is performed without solvent. In many cases imidazole crystallizes from the solvent free Silicon-Urea-Azolides during standing. The product can be filtered or washed or cleaned in any other desired way. However, generally filtered silicone urea azolide is ready for use for most purposes. Sometimes even filtration can be done without, especially if a thermolytic decomposition leading to Silicone-Isocyanate is desired.

Reaction times can be varied. It has proven to be advantageous to let the reaction run between about 0.5 to about 50, e.g., between about 1 and about 30 h, or between about 2 to about 20 h or about 5 to about 10 h. If the Silicone-Urea-Azolide is not going to be isolated, the reaction time can basically be chosen freely.

The invention also relates to a process for the production of an Silicone-Urea-Azolide according to the general formula (I) wherein an amino compound according to the general formula $(H(R^4)N)_n X$, X being a monomeric, oligomeric or polymeric radical with the functionality n containing at least one Si atom and n is 1 to about 100000, is reacted in one or more steps with one or more compounds to form an azolide according to formula (I).

In the inventive process, an amino compound according to the general formula $(H(R^4)N)_n X$ is preferably reacted with a compound according to the general formula

with A being an azole ring connected to the carbonyl group via an N atom or where the amino compound according to the general formula $(H(R^4)N)_n X$ is reacted in a first step with phosgene, optionally together with a trialkylamine and in a second step with an azole under formation of an Silicone-Urea-Azolide according to general formula (I).

The amino compound preferably comprises at least one or more features selected from the following group of features:
a) at least one Si—O—Si bond,
b) one or more groups $HN(R^4)$— (as defined in formula (I)) connected to Si atom(s) via an organic spacer,
c) no additional nucleophilic functional groups capable of reacting with isocyanates at room temperature faster than the NH-bond in a urea group (e.g. OH—, NH—, SH—, COOH—).

It can further be preferred if an amino compound comprises one or more of the following silicone structures:
a) Linear or branched $(R^1{}_2R^2SiO_{1/2})_2(R^1R^2SiO_{2/2})_x$ where $R^1$ independently is H, or a linear, branched, cyclic or aromatic saturated or unsaturated facultatively partly or fully fluorinated organic residue with 1 to 30 C-atoms that may contain 0 to 5 O atoms; $R^2$ independently is $R^1$ but at least one $R^2$ group up to all $R^2$ groups is/are $R^3$—NH—C(=O)-A; $R^3$ is a bifunctional organic radical alkylene, arylene or mixed with 1 to 18 carbon atoms that may contain 0 to 5 O atoms; A is an azole ring; the linear chain may be branched by up to 5 moieties of the structure $R^2SiO_{2/2}$ and/or $SiO_{4/2}$; x=0 to 100000;
b) cyclic $(R^1R^2SiO_{2/2})_m$ where $R^1$ independently is H, or a linear, branched, cyclic or aromatic saturated or unsaturated facultatively partly or fully fluorinated organic residue with 1 to 30 C-atoms that may contain 0 to 5 O atoms; $R^2$ independently is $R^1$ but at least one $R^2$ group up to all $R^2$ groups is/are $R^3$—NH—C(=O)-A; $R^3$ is a bifunctional organic radical alkylene, arylene or mixed with 1 to 18 carbon atoms that may contain 0 to 5 O atoms; A is an azole ring; m=3 to 1000;
c) polycyclic $(R^2SiO_{3/2})_o$, or $(R^1{}_2R^2SiO_{1/2})_p(SiO_{4/2})_q$ where $R^1$ independently is H, or a linear, branched, cyclic or aromatic saturated or unsaturated facultatively partly or fully fluorinated organic residue with 1 to 30 C-atoms that may contain 0 to 5 O atoms; $R^2$ independently is $R^1$ but at least one $R^2$ group up to all $R^2$ groups is/are $R^3$—NH—C(=O)-A; $R^3$ is a bifunctional organic radical alkylene, arylene or mixed with 1 to 18 carbon atoms that may contain 0 to 5 O atoms; A is an azole ring; o is 6 to 100000 p=1 to q and q is 6 to 100000.

It can be preferred, if A independently is selected from the group consisting of pyrazole, imidazole, triazole, benzimidazole, benzotriazole, tetrazole, especially imidazole, triazole, benzimidazole, benzotriazole.

In a process according to the invention, the molar ratio of amino groups to carbonyl-bisazolide can generally be chosen freely. However, good results have, e.g., been achieved when the molar ratio of amino groups to carbonyl-bisazolide is in the range of about 1:2 to about 1:1.

Generally, any type of solvent can be used in the inventive process which does not detrimentally influence the process itself. It can be preferred, if a solvent or solvent mixture is used that compatibalizes amino compound and carbonyl-bisazolide or if a solvent or solvent mixture is used that does not or not fully compatibalizes amino compound and carbonyl-bisazolide. It is also possible not to use any solvent at all.

Silicon-Urea-Azolides can be dissociated by application of heat to give Silicone-Isocyanates and azoles. The Silicone-Isocyanates can be obtained by separation of the azole from the equilibrium. This can be done most conveniently by using a thin film evaporator or a short path distiller where pyrolytic decomposition and removal of the azole generated can be achieved conveniently by applying vacuum.

When using a short path distillator, it has proven to be successful when the temperature of the feed is at about −50 to about 200° C. or at about −20 to about 150° C. or at about 0 to about 100° C. or at about 10 to about 70° C., the temperature of the evaporator is at about 50 to about 300° C. or at about 70 to about 250° C. or at about 80 to about 200° C. or at about 90 to about 180° C. and the temperature of the collector is at about −50 to about 200° C. or at about 0 to about 150° C. or at about 20 to about 100° C. or at about 30 to about 90° C.

Another way to obtain the isocyanates, can be to shock-freeze a heated silicone urea azolide and thereby force the azolide to crystallize which removes the azolide from the equilibrium. Filtration or centrifugation can also be used to separate the crystallized azole. Whereas regardless of the process chosen in many cases one decomposition and separation step is sufficient to obtain satisfactory product quality in some cases multiple repetition can be advantageous to obtain the desired purity.

Silicon-Urea-Azolides are useful compounds. In most cases they react the same way the corresponding isocyanates do, although noticeably slower. For this reason, however, Silicone-Urea-Azolides cannot be considered as "blocked" or "capped" isocyanates because those at room temperature should usually be unreactive and only by thermal activation react as isocyanates.

The described Silicone-Urea-Azolides are useful for many different purposes. It has, e.g., proven to be expedient to use the Silicone-Urea-Azolides for the production of Silicone-Isocyanates. The invention thus also relates to a process for production of Silicone-Isocyanates wherein a Silicone-Urea-Azolide is decomposed at an elevated temperature. It has further proven to be possible and successful, if the product is not isolated after completion of the reaction but the produced Silicone-Isocyanate and the Azole are separated at decomposition temperature. It is thus a preferred feature of the process for the production of Silicone-Isocyanates that the decomposition of the Silicone-Urea-Azolide is accompanied by separation of the products Silicone-Isocyanate and azole at decomposition temperature.

The resulting Azole can preferably be removed under vacuum. In the inventive process, it can further be preferred, if at one point within a matrix of temperature and pressure defined between 60° C. to 180° C. and $10^{-5}$ mbar to 200 mbar predominantly Azole and Silicone-Isocyanate are produced.

The invention thus not only relates to the production of Silicone-Urea-Azolide and the subsequent generation of Silicone-Isocyanate in a successive step. The invention also relates to a process for the production of a Silicone-Isocyanate, wherein a mixture of Silicone-Amine and A-C(=O)-A is reacted and decomposed to form Silicone-Isocyanate without isolating the intermediate Silicone-Urea-Azolide. In can be preferred, if this reaction is performed without using a solvent.

The yield of this process for the production of Silicone-Isocyanate is generally above about 80%, in many cases yields of more than 90% or more than 95% can be obtained. It is noteworthy that the obtained Silicone-Isocyanate generally is comparatively pure. Due to the reaction path it is generally essentially free of heavy metals and noble metals. Preferably, the Silicone-Isocyanate contains less than 100 ppm by weight or less than 50 ppm by weight or less than 10 ppm by weight of one or more noble metals, preferably Pt. In the Silicone-Isocyanate the content of Azolide, given by the weight of the residue A of formula (I) is generally between about 50 ppm and about 1%, preferably below 0.5 or below 0.1 or below 0.05%. It is preferred if the obtained Silicone-Isocyanate contains at least about 50 or about 100 ppm or about 200 ppm of Azole or at least about 50 or about 100 ppm or about 200 ppm of Azolide or both.

The Silicone-Urea-Azolides and the Silicone-Isocyanates according to the invention or produced according to the invention can generally be used for the production of different types of materials or in different types of processes, e.g., industrial or dental/healthcare, or the like. Generally, the Silicone-Urea-Azolides and the Silicone-Isocyanates according to the invention or produced according to the invention can be employed in any process where conventional Silicone-Isocyanates have been used. Thus, the Silicone-Urea-Azolides and the Silicone-Isocyanates according to the invention or produced according to the invention can be used for the production of any type of three dimensional object or can be used in the field of adhesives.

The preparations can especially be used in very different dental materials employed in dental medicine or dental technology. Preferred areas of use of such dental materials are single-phase and two-phase impression-taking in dental medicine and bite registration.

The invention is further illustrated by way of examples.

EXAMPLES

All procedures are performed under dry nitrogen. All Short Path Distillations performed an a KDL 5 (UIC GmbH, Am neuen Berg 4, D-63755 Alzenau-Hörstein) Short Path Distillator.

CDI: Carbonyl-bisimidazolide, a carbonyl bisazolide with CAS-#: [530-62-1]

All procedures are performed under dry nitrogen. All Short Path Distillations performed on a KDL 5 (UIC GmbH, Am Neuen Berg 4, D-63755 Alzenau-Hörstein) Short Path Distillator. Yields can be generally diminished by losses due to stripping of low molecular contents and due to manipulation and residues in the apparatus.

Although mass yields in some cases are only moderate due to losses in the apparatus, the degree of functionalization usually is substantially greater than 90% (if not indicated otherwise).

Example 1

Silicone-Urea-Azolide

At room temperature 24.32 g (0.15 Mole) CDI (FULKA, >97%) are dispersed in 500 ml Cyclohexane. 50 ml dry THF are added. 177.2 g (30 mMole) PDMS diamine (3M St. Paul, M: 5.740) are added to the suspension under stirring within 90 min. After one additional hour of stirring the suspension is filtrated and the clear slightly viscous liquid is washed 3 times with 250 ml of water dried with $Na_2SO_4$ filtrated again and evaporated from the solvent. Clear off-white to amber liquid is obtained. Yield: 171.9 g (97% of theory); Viscosity: 1.2 Pa*s; $^1$H NMR δ ($C\underline{H}_2$—N(H)C(O)—): 3.45 ppm (vs. TMS in $CDCl_3$).

Example 2

Silicone-Isocyanate 140 g of 1 are passed over a KDL 5 Short Path Distillator at

| $T_{(Feed)}$: | 50° C. | Pressure: | 1 mbar |
|---|---|---|---|
| $T_{(Evaporator)}$: | 120° C. | Duration: | 3 h |
| $T_{(Collector)}$: | 50° C. | | |

During the reaction imidazole crystallizes at the central cooler, while clear liquid product is collected. Clear off-white to amber liquid is obtained. Yield: 130.7 g (96% of theory); Viscosity: 0.2 Pa*s; NCO-Equivalent: 3.580 g/Mole; $^1$H NMR δ ($C\underline{H}_2$—NCO): 3.24 ppm (vs. TMS in $CDCl_3$).

Example 3

Silicone-Urea-Azolide

At room temperature 39.1 g (0.241 Mole) CDI (FLUKA, >97%) are dispersed in 250 ml Cyclohexane and 150 ml dry THF. Temperature drops as part of CDI dissolves. 400 g (80.3 mMole) PDMS diamine (Clariant 66M66, M: 4.980) are added to the suspension under stirring within 90 min. After one additional hour of stirring the suspension is filtrated and diluted with 500 ml Cyclohexane. The clear slightly viscous liquid is washed 5 times with 100 ml of water dried with $Na_2SO_4$ filtrated again and evaporated from the solvent. Clear off-white to amber liquid is obtained. Yield: 371 g (89% of theory); Viscosity: 1.2 Pa*s; $^1$H NMR δ ($C\underline{H}_2$—N(H)C(O)—): 3.45 ppm (vs. TMS in $CDCl_3$).

Example 4

Silicone-Urea-Azolide

At room temperature 25 g (0.152 Mole) 1,1'-Carbonyldi-(1,2,4)-triazol CAS-#[41864-22-6] (CDT, FLUKA, ~95%) are dispersed in 200 ml dry THF. Temperature drops as part of CDT dissolves. 285.7 g (100 mMole) PDMS diamine (3M St. Paul, M: 5.710) are dissolved in 200 ml Cyclohexane and added to the suspension under stirring within 90 min. After additional 16 hours of stirring the suspension is diluted with 300 ml Cyclohexane and filtrated. The clear filtrate is evaporated from the solvent. Clear pale yellow liquid is obtained. Yield: 272.5 g (93% of theory); Viscosity: 0.24 Pa*s; $^1$H NMR δ ($\underline{CH_2}$—N(H)C(O)—): 3.41 ppm (vs. TMS in CDCl$_3$).

Example 5

Silicone-Isocyanate 250 g of 4 are passed over a KDL 5 Short Path Distillator at

| $T_{(Feed)}$: | 30° C. | Pressure: | $10^{-5}$ mbar |
|---|---|---|---|
| $T_{(Evaporator)}$: | 140° C. | Throughput: | 100 g/h |
| $T_{(Collector)}$: | 60° C. | Agitation: | 400 rpm |

During the reaction little triazole crystallizes at the central cooler, white clear liquid product is collected. Clear off-white to amber liquid is obtained. $^1$H NMR shows that only ~16% of azolide has been converted to Isocyanate.

Example 6

Silicone-Urea-Azolide

6a: At room temperature 15.9 g (0.098 Mole) CDI (FLUKA, >97%) are dispersed in 500 ml Cyclohexane and 50 ml dry THF. 500 g (39.13 mMole) PDMS diamine (ABCR, DMS-A32, M: 25.550) are added to the suspension under stirring within 60 min. After additional 16 hours of stirring the suspension is diluted with 500 ml Cyclohexane and filtrated. The clear filtrate is evaporated from the solvent. Clear pale yellow liquid is obtained. Yield: 500.5 g (99% of theory); Viscosity: 9.9 Pa*s; $^1$H NMR δ ($\underline{CH_2}$—N(H)C(O)—): 3.45 ppm (vs. TMS in CDCl$_3$).

6b: Reproduction of the experiment: Yield: 500 g (99% of theory); Viscosity: 10.6 Pa*s; $^1$H NMR δ ($\underline{CH_2}$—N(H)C(O)—): 3.47 ppm (vs. TMS in CDCl$_3$).

Example 7

Silicone-Isocyanate

7a: 500 g of 6a are passed over a KDL 5 Short Path Distillator at

| $T_{(Feed)}$: | 60° C. | Pressure: | $2 \times 10^{-2}$ mbar |
|---|---|---|---|
| $T_{(Evaporator)}$: | 120° C. | Duration: | 3 h |
| $T_{(Collector)}$: | 60° C. | | |

During the reaction imidazole crystallizes at the central cooler, while clear liquid product is collected. Clear off-white to amber liquid is obtained. Yield: 452.4 g (91% of theory); Viscosity: 3.8 Pa*s; NCO-Equivalent: 16.050 g/Mole; $^1$H NMR δ ($\underline{CH_2}$—NCO): 3.30 ppm (vs. TMS in CDCl$_3$).

7b: 500 g of 6b are passed two times over a KDL 5 Short Path Distillator at

| $T_{(Feed)}$: | 23° C. | Pressure: | $10^{-2}$ mbar |
|---|---|---|---|
| $T_{(Evaporator)}$: | 120° C. | Duration: | 3 h |
| $T_{(Collector)}$: | 80° C. | Agitation: | 480 rpm |

During the reaction imidazole crystallizes at the central cooler, while clear liquid product is collected. Clear off-white to amber liquid is obtained. Yield: 415 g (83% of theory); Viscosity: 3.8 Pa*s; NCO-Quivalent: 15.170 g/Mole; Refractive index ($n_D^{20}$): 1.4065; $^1$H NMR δ ($\underline{CH_2}$—NCO): 3.30 pm (vs. TMS in CDCl$_3$).

Example 8

Silicone-Urea-Azolide

At room temperature 32.42 g (0.20 Mole) CDI (FLUKA, >97%) are dispersed in 150 ml Toluene. At RT 24.85 g (0.10 Mole) 1,3,-Bis-(3-aminopropyl)-1,1,3,3-tetramethyldisiloxane (Lancaster 97%) are added to the suspension under stirring within 30 min. During addition temperature of the reaction mixture is kept at 23° C. with an ice bath. After addition a clear two phase reaction mixture remains. The lower layer is separated and solvent is removed. Clear brownish yellow oil is obtained. Yield: 58.5 g (with imidazole and traces of toluene); $^1$H NMR δ ($\underline{CH_2}$—N(H)C(O)—): 3.50 ppm (vs. TMS in CDCl$_3$).

Example 9

Silicone-Urea-Azolide

At room temperature 60.81 g (0.375 Mole) CDI (FLUKA, >97%) are dispersed in 500 ml dry THF. 282.25 g (250 mEquivalent) (3-aminopropyl-methylsiloxan)-(dimenthylsiloxan)copolymer (ABCR, AMS-162, Base-Equivalent: 1.129) are added to the suspension under stirring within 180 min. After additional 3 hours of stirring the suspension is filtrated and evaporated from the solvent. The remaining suspension is diluted with 500 ml Cyclohexane and filtrated again. The clear filtrate is evaporated from the solvent. Clear yellow liquid is obtained. Yield: 286.1 g (99% of theory); Viscosity: 5.3 Pa*s; Refractive index ($n_D^{20}$): 1.4301; $^1$H NMR δ ($\underline{CH_2}$—N(H)C(O)—): 3.42 ppm (vs. TMS in CDCl$_3$).

Example 10

Silicone-Isocyanate 250 g of 9 are passed over a KDL 5 Short Path Distillator at

| $T_{(Feed)}$: | 50° C. | Pressure: | $2 \times 10^{-2}$ mbar |
|---|---|---|---|
| $T_{(Evaporator)}$: | 150° C. | Feed: | 150 g/h |
| $T_{(Collector)}$: | 70° C. | Agitation: | 500 rpm |

During the reaction imidazole crystallizes at the central cooler, while clear liquid product is collected. Clear off-white to amber liquid is obtained. Yield: 216.5 g (91% of theory); Viscosity: 0.25 Pa*s; NCO-Equivalent: 1.480 g/Mole; $^1$H NMR δ ($\underline{CH_2}$—NCO): 3.29 ppm (vs. TMS in CDCl$_3$).

Example 11

Silicone-Urea-Azolide

At room temperature 16.2 g (0.100 Mole) CDI (FLUKA, >97%) are placed in a dry round bottom flask at RT. The flask is immersed into an ice-bath and 119 g (25 mMole) PDMS diamine (ABCR, DMS-A21, M: 4760) are added under stirring within 10 min. After additional 4 days of stirring the suspension is filtrated. Clear yellow liquid is obtained. Yield: 99.3 g (80% of theory); Viscosity: 1.7 Pa*s; Refractive index $(n_D^{20})$: 1.4162; $^1$H NMR δ (C$\underline{H}_2$—N(H)C(O)—): 3.47 ppm (vs. TMS in CDCl$_3$).

Example 12

Silicone-Isocyanate 85 g of 11 are passed over a KDL 5 Short Path Distillator at

| $T_{(Feed)}$: | 40° C. | Pressure: | $2 \times 10^{-2}$ mbar |
|---|---|---|---|
| $T_{(Evaporator)}$: | 130° C. | Feed: | 150 g/h |
| $T_{(Collector)}$: | 70° C. | Agitation: | 500 rpm |

During the reaction imidazole crystallizes at the central cooler, while clear liquid product is collected. Clear off-white to amber liquid is obtained. Yield: 78 g (96% of theory); Viscosity: 0.17 Pa*s; NCO-Equivalent: 3.120 g/Mole; $^1$H NMR δ (C$\underline{H}_2$—NCO): 3.30 ppm (vs. TMS in CDCl$_3$).

Example 13

Silicone-Urea-Azolide

At room temperature 52.45 g (0.20 Mole) 1,1'-Carbonyldibenzimidazol (CDBI) CAS-#: [14667-54-0] (prepared from phosgene and benzimidazole; >95%) are dispersed in 250 ml Cyclohexane and 25 ml dry THF. Temperature drops as part of CDBI dissolves to give a white viscous suspension. 238.1 g (50 mMole) PDMS diamine (ABCR DMS-A21, M: 4760) are added to the suspension under stirring within 60 min. After additional 16 hours of stirring the suspension is filtrated. The clear filtrate is evaporated form the solvent. Clear pale yellow liquid is obtained. Yield: 250.5 g (99% of theory); Viscosity: 2.0 Pa*s; Refractive index $(n_D^{20})$: 1.421; $^1$H NMR δ (C$\underline{H}_2$—N(H)C(O)—): 3.54 ppm (vs. TMS in CDCl$_3$).

Example 14

Silicone-Isocyanate

First run: 230 g of 13 are passed over a KDL 5 Short Path Distillator at

| $T_{(Feed)}$: | 50° C. | Pressure: | $2 \times 10^{-2}$ mbar |
|---|---|---|---|
| $T_{(Evaporator)}$: | 140° C. | Feed: | 150 g/h |
| $T_{(Collector)}$: | 80° C. | Agitation: | 500 rpm |

During the reaction imidazole crystallizes at the central cooler, while clear liquid product is collected. Clear off-white to amber liquid is obtained. Yield: 223 g (97% of theory); Viscosity: 0.49 Pa*s; NCO-Equivalent: 4.710 g/Mole; Refractive index $(n_D^{20})$: 1.4153; $^1$H NMR δ (C$\underline{H}_2$—NCO): 3.30 ppm (vs. TMS in CDCl$_3$) still azolide present (~30%).

Second run: 190 g of first run product are passed over a KDL 5 Short Path Distillator at

| $T_{(Feed)}$: | 50° C. | Pressure: | $2 \times 10^{-2}$ mbar |
|---|---|---|---|
| $T_{(Evaporator)}$: | 140° C. | Feed: | 150 g/h |
| $T_{(Collector)}$: | 80° C. | Agitation: | 500 rpm |

During the reaction imidazole crystallizes at the central cooler, while clear liquid product is collected. Clear off-white to amber liquid is obtained. Yield: 189 g (95% of theory); Viscosit<0.229 Pa*s; NCO-Equivalent: 3.830 g/Mole; Refractive index $(n_D^{20})$: 1.4110; $^1$H NMR δ (C$\underline{H}_2$—NCO): 3.30 ppm (vs. TMS in CDCl$_3$).

Example 15

Silicone-Urea-Azolide

At room temperature 34 g (0.21 Mole)CDI (FLUKA, >97%) are dispersed in 250 ml Cyclohexane and 25 ml dry THF. Temperature drops as part of CDI dissolves to give a white suspension. The flask is immersed into an ice-bath and 238.1 g (50 mMole) PDMS diamine (ABCR, DMS-A21, M: 4760) are added under stirring within 30 min. After additional 16 hours of stirring the suspension is filtrated. The clear filtrate is evaporated form the solvent. Clear pale yellow liquid is obtained. Yield: 249.6 g (101% of theory); Viscosity: 1.7 Pa*s; Refractive index $(n_D^{20})$: 1.4173; $^1$H NMR δ (C$\underline{H}_2$—N(H)C(O)—): 3.50 ppm (vs. TMS in CDCl$_3$); Chlorine content: 633 ppm.

Example 16

Silicone-Isocyanate 238 g of 15 are passed over a KDL 5 Short Path Distillator at

| $T_{(Feed)}$: | 40° C. | Pressure: | $2 \times 10^{-2}$ mbar |
|---|---|---|---|
| $T_{(Evaporator)}$: | 130° C. | Feed: | 150 g/h |
| $T_{(Collector)}$: | 70° C. | Agitation: | 500 rpm |

During the reaction imidazole crystallizes at the central cooler, while clear liquid product is collected. Clear off-white to amber liquid is obtained. Yield: 210 g (88% of theory); Viscosity: 0.17 Pa*s; NCO-equivalent: 3.026 g/Mole; $^1$H NMR δ (C$\underline{H}_2$—NC): 3.30 ppm (vs. TMS in CDCl$_3$); Refractive index $(n_D^{20})$: 1.4095; Chlorine content: 27 ppm.

Example 17

Silicone-Urea-Azolide

In a dry round bottom flask at room temperature 24.73 g (0.05 Mole) Phosgene in toluene (~20%, FLUKA, contains 4.95 g COCl$_2$) are dissolved in additional 100 ml of toluene. Within 60 min at 5° C. and cooling a mixture of 119.05 g (25 mMole) PDMS diamine (ABCR, DMS-A21, M: 4760) and 10.12 g Triethylamine (100 mMole, ACROS, >99%) and 150 ml toluene are added under stirring within 60 min. Temperature stays below 8° C. and Triethylamine hydrochloride precipitates. The suspension is stirring an additional hour at 8° C.

At 5° C. to the obtained suspension containing PDMS chloroformic amide a solution of 3.472 g imidazole (51 mMole; ACROS>99%), and 5.06 g Triethylamine (50 mMole, ACROS, >99%) in 50 ml acetone is added within 10 minutes. Temperature rises to 10° C. where the mixture is stirred additional 2 hours. Temperature rises slowly to RT during additional 16 hours of stirring whereafter the suspension is filtrated. The clear filtrate is evaporated from the solvent. Clear pale yellow liquid is obtained. Yield: 118.4 g (96% of theory); Viscosity: 2.5 Pa*s; $^1$H NMR δ (C$\underline{H}_2$—N(H)C(O)—): 3.45 ppm (vs. TMS in CDCl$_3$); Chlorine content: 1100 ppm.

Example 18

Silicone-Isocyanate 100 g of 17 are passed over a KDL 5 Short Path Distillator at

| | | | |
|---|---|---|---|
| $T_{(Feed)}$: | 40° C. | Pressure: | $2 \times 10^{-2}$ mbar |
| $T_{(Evaporator)}$: | 130° C. | Feed: | 150 g/h |
| $T_{(Collector)}$: | 70° C. | Agitation: | 500 rpm |

During the reaction imidazole crystallizes at the central cooler, while clear liquid product is collected. Clear off-white to amber liquid is obtained. Yield: 78.7 g (81% of theory); Viscosity: 0.38 Pa*s; NCO-Equivalent: 3.814 g/Mole; $^1$H NMR δ (CH$_2$—NCO): 3.30 ppm (vs. TMS in CDCL$_3$) with noticeable chain extension; Refractive index ($n_D^{20}$): 1.4094; Chlorine content: 19 ppm.

Example 19

Silicone-Urea-Azolide

At room temperature 21 g (0.130 Mole) CDI (FLUKA, >97%) are dispersed in 250 ml Cyclohexane and 25 ml dry THF. Temperature drops as part of CDI dissolves to give a white suspension. The flask is immersed into an ice-bath and 1000 g (113 mMole) PDMS diamine (3M, base equivalent 17710 g/Mole) are added under stirring within 120 min. After additional 16 hours of stirring the suspension is filtrated. The clear filtrate is evaporated form the solvent. Clear pale yellow liquid is obtained. Yield: 1000.1 g (99.5% of theory); Viscosity: 21.9 Pa*s; Refractive index ($n_D^{20}$): 1.4072; $^1$H NMR δ (C$\underline{H}_2$—N(H)C(O)—): 3.50 ppm (vs. TMS in CDCl$_3$).

Example 20

Silicone-Isocyanate 1000 g of 19 are passed over a KDL 5 Short Path Distillator at

| | | | |
|---|---|---|---|
| $T_{(Feed)}$: | 40° C. | Pressure: | $2 \times 10^{-2}$ mbar |
| $T_{(Evaporator)}$: | 130° C. | Feed: | 200 g/h |
| $T_{(Collector)}$: | 90° C. | Agitation: | 500 rpm |

During the reaction imidazole crystallizes at the central cooler, while clear liquid product is collected. Clear off-white to amber liquid is obtained. Yield: 880 g (88% of theory); Viscosity: 8.4 Pa*s; NCO-Equivalent: 18825 g/Mole; $^1$H NMR δ (CH$_2$—NCO): 3.30 ppm (vs. TMS in CDCl$_3$); Refractive index ($n_D^{20}$): 1.4060.

Example 21

Silicone-Urea-Azolide

At room temperature 8.51 g (0.0525 Mole) CDI (FLUKA, >97%) are dispersed in 120 ml Cyclohexane and 12 ml dry THF. Temperature drops as part of CDI dissolves to give a white suspension. The flask is immersed into an ice-bath and 119 g (50 mEquivalent) PDMS diamine (ABCR, base equivalent 2381 g/Mole) are added under stirring within 120 min. After additional 16 hours of stirring the suspension is filtrated. The clear filtrate is evaporated from the solvent. Clear pale yellow liquid is obtained. Yield: 118 g (97% of theory); Viscosity: 1.40 Pa*s; Refractive index ($n_D^{20}$): 1.4166; $^1$H NMR δ (CH$_2$—N(H)C(O)—): 3.50 ppm (vs. TMS in CDCl$_3$); Chlorine content: 191 ppm.

Example 22

Silicone-Isocyanate 118 g of 21 are passed over a KDL 5 Short Path Distillator at

| | | | |
|---|---|---|---|
| $T_{(Feed)}$: | 23° C. | Pressure: | $2 \times 10^{-2}$ mbar |
| $T_{(Evaporator)}$: | 130° C. | Feed: | 100 g/h |
| $T_{(Collector)}$: | 90° C. | Agitation: | 500 rpm |

During the reaction imidazole crystallizes at the central cooler, while clear liquid product is collected. Clear off-white to amber liquid is obtained. Yield: 76 g; Viscosity: 0.16 Pa*s; NCO-Equivalent: 2965 g/Mole; $^1$H NMR δ (CH$_2$—NCO): 3.30 ppm (vs. TMS in CDCl$_3$); Refractive index ($n_D^{20}$): 1.409.

Example 23

Silicone-Urea-Azolide

At room temperature 151.54 g (0.935 Mole)CDI (FLUKA, >97%) are dispersed in 1000 ml Cyclohexane and 100 ml dry THF. Temperature drops as part of CDI dissolves to give a white suspension. The flask is immersed into an ice-bath and 200 g (467.3 mEquivalent) PDMS diamine (ABCR, base equivalent 428 g/Mole) are added under stirring within 120 min. After additional 16 hours of stirring the suspension is filtrated. The clear filtrate is evaporated from the solvent. After filtration clear pale yellow liquid is obtained. Yield: 230 g; Viscosity: 2.2 Pa*s; Refractive index ($n_D^{20}$): 1.4579; $^1$H NMR δ (CH$_2$—N(H)C(O)—): 3.50 ppm (vs. TMS in CDCl$_3$).

Example 24

Silicone-Isocyanate 230 g of 23 are passed over a KDL 5 Short Path Distillator (first run) at

| | | | |
|---|---|---|---|
| $T_{(Feed)}$: | 23° C. | Pressure: | $2 \times 10^{-2}$ mbar |
| $T_{(Evaporator)}$: | 140° C. | Feed: | 80 g/h |
| $T_{(Collector)}$: | 90° C. | Agitation: | 500 rpm |

During the reaction imidazole crystallizes at the central cooler, while clear liquid product is collected. Clear off-white to amber liquid is obtained. Yield: 96.2 g residual 10% of imidazolide.

Second run under same conditions using material form first run: Yield: 90 g; Viscosity: 0.023 Pa*s; NCO-Equivalent: 820 g/Mole; $^1$H NMR δ (CH$_2$—NCO): 3.30 ppm (vs. TMS in CDCl$_3$); Refractive index ($n_D^{20}$): 1.4157.

Example 25

Silicone-Isocyanate

At room temperature 17 g (0.1048 Mole) CDI (FLUKA, >97%) are dispersed in 238.1 g (100 mEquivalent) PDMS diamine (ABCR, base equivalent 2381 g/Mole) are added under stirring in one portion. The off-white suspension shows self-hating and is passed over a KDL 5 Short Path Distillator (first run) while stirring at

| | | | |
|---|---|---|---|
| $T_{(Feed)}$: | 25-55° C. | Pressure: | $2 \times 10^{-2}$ mbar |
| $T_{(Evaporator)}$: | 140° C. | Feed: | 150 g/h |
| $T_{(Collector)}$: | 90° C. | Agitation: | 500 rpm |

During the reaction imidazole crystallizes at the central cooler, while clear liquid product is collected. Clear off-white to amber liquid is obtained. Yield: 219 g residual 10% of imidazolide. Second run under same conditions using material from first run: Yield: 212 g; Viscosity: 0.46 Pa*s; NCO-Equivalent; 4650 g/Mole; $^1$H NMR δ (CH$_2$—NCO): 3.30 ppm (vs. TMS in CDCl$_3$) about 20 to 30% chain extension; Refractive index ($n_D^{20}$): 1.410.

The invention claimed is:

1. A process for the production of an azolide according to the general formula I

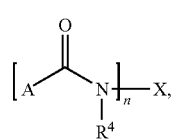

(I)

wherein A is an azole ring connected to the carbonyl group via an N atom, R$^4$ is H or a linear or branched or cyclic alkyl group with 1 to 24 C-atoms, X is an oligomeric or polymeric radical with the functionality n, wherein n is 1 to about 100000, having a molecular weight of at least 200 and at least 2 repetition units with at least 1 Si-atom per repetition unit, wherein an amino compound according to the general formula (H$_2$N—)$_n$X is reacted in a first step with phosgene, optionally together with a trialkylamine, and in a second step with an azole to form an azolide according to formula I, wherein the azolide thermally decomposes at least at one point within a matrix of temperature and pressure defined between about 60° C. to about 180° C. and about $10^{-5}$ mbar to about 200 mbar resulting in predominantly Azole and Silicone-Isocyanate;

wherein the azolide comprises one or more of the following silicone structures:

a) linear or branched $(R^1{}_2R^2SiO_{1/2})_2(R^1R^2SiO_{2/2})_x$ where R$^1$ independently is H, or a linear, branched, cyclic or aromatic saturated or unsaturated facultatively partly or fully fluorinated organic residue with 1 to 30 C-atoms that may contain 0 to 5 O atoms; R$^2$ independently is R$^1$ but at least one R$^2$ group up to all R$^2$ groups is/are R$^3$—NH—C(=O)-A; R$^3$ is a bifunctional organic radical alkylene, arylene or mixed with 1 to 18 carbon atoms that may contain 0 to 5 O atoms; A is an azole ring; the linear chain may be branched by up to 5 moieties of the structure R$^2$SiO$_{2/2}$ and/or SiO$_{4/2}$, x=0 to 100000;

b) cyclic $(R^1R^2SiO_{2/2})$m where R$^1$ independently is H, or a linear, branched, cyclic or aromatic saturated or unsaturated facultatively partly or fully fluorinated organic residue with 1 to 30 C-atoms that may contain 0 to 5 O atoms; R$^2$ independently is R$^1$ but at least one R$^2$ group up to all R$^2$ groups is/are R$^3$—NH—C(=P)-A; R$^3$ is a bifunctional organic radical alkylene, arylene or mixed with 1 to 18 carbon atoms that may contain 0 to 5 O atoms; A is an azole ring; M=3 to 1000;

c) polycyclic $(R^2SiO_{3/2})_o$, or $(R^1{}_2R^2SiO_{1/2})_p(SiO_{4/2})_q$ where R$^1$ independently is H, or a linear, branched, cyclic or aromatic saturated or unsaturated facultatively partly or fully fluorinated organic residue with 1 to 30 C-atoms that may contain 0 to 5 O atoms; R$^2$ independently is R$^1$ but at least one R$^2$ group up to all R$^2$ groups is/are R$^3$—NH—C(=O)-A; R$^3$ is a bifunctional organic radical alkylene, arylene or mixed with 1 to 18 carbon atoms that may contain 0 to 5 O atoms; A is an azole ring; o is 6 to 100000 p=1 to q and q is 6 to 100000.

2. A process for the production of Silicone-Isocyanates, wherein an azolide according to the general formula I

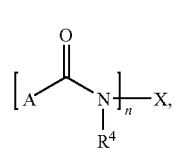

(I)

wherein A is an azole ring connected to the carbonyl group via an N atom, R$^4$ is H or a linear or branched or cyclic alkyl group with 1 to 24 C-atoms, X is silicone oligomeric or polymeric radical with the functionality n, wherein n is 1 to about 100000, having a molecular weight of at least 200 and at least 2 repetition units with at least 1 Si-atom per repetition unit, is decomposed at elevated temperatures.

3. The process according to claim 2, wherein the decomposition under formation of an isocyanate and an azole takes place in the absence of solvent.

4. The process according to claim 2, wherein the azole is removed under vacuum.

5. The process according to claim 2, wherein the decomposition takes place at a temperature in a range of about 60 to about 180° C. or at a pressure of from about $1*10^{-5}$ mbar to about 200 mbar or both.

6. The process according to claim 2, wherein the decomposition under formation of an isocyanate and an azole takes place in the absence of solvent and the azole is removed under vacuum.

7. A process for the production of a Silicone-Isocyanate, wherein a mixture of Silicone-Amine and A-C(=O)-A is reacted and decomposed to form Silicone-Isocyanate without isolating an intermediate Silicone-Urea-Azolide, wherein A is an azole ring connected to the carbonyl group via an N atom or where an amino compound according to the formula $(H_2N—)_nX$ is reacted in a first step with phosgene, optionally together with a trialkylamine, and in a second step with an azole under formation of an azolide according to the general formula I:

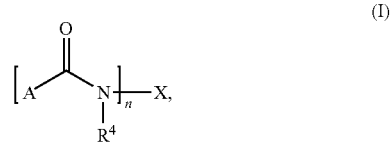

(I)

wherein A is an azole ring connected to the carbonyl group via an N atom, $R^4$ is H or a linear or branched or cyclic alkyl group with 1 to 24 C-atoms, X is an oligomeric or polymeric radical with the functionality n, wherein n is 1 to about 100000, having a molecular weight of at least 200 and at least 2 repetition units with at least 1 Si-atom per repetition unit to form an intermediate that is further decomposed at elevated temperatures to form Silicone-Isocyanate.

8. The process according to claim 7, wherein the reaction and decomposition is performed in the absence of a solvent.

* * * * *

UNITED STATES PATENT AND TRADEMARK OFFICE
CERTIFICATE OF CORRECTION

PATENT NO. : 8,124,714 B2
APPLICATION NO. : 12/091552
DATED : February 28, 2012
INVENTOR(S) : Peter Bissinger It is certified that error appears in the above-identified patent and that said Letters Patent is hereby corrected as shown below:

Column 1
Line 32 (Approx.)         Delete "insoluble" and insert -- isolable --, therefor.

Column 2
Line 24 (Approx.)         Delete "imidazol." and insert -- imidazole. --, therefor.

Column 4
Line 24                   Delete "catalysts" and insert -- catalysts. --, therefor.
Line 32                   Delete "applicability" and insert -- applicability. --, therefor.
Lines 37-38               Delete "Engeneering"" and insert -- Engineering" --, therefor.

Column 6
Line 1                    Delete "alkylen, arylen" and insert -- alkylene, arylene --, therefor.
Line 16                   Delete "$R^2SiO_{22}$" and insert -- $R^2SiO_{2/2}$ --, therefor.
Line 40                   Delete "trifluormethyl," and insert -- trifluoromethyl, --, therefor.
Line 51                   Delete "trifluormethyl," and insert -- trifluoromethyl, --, therefor.

Column 7
Line 7                    Delete "an" and insert -- on --, therefor.
Line 21 (Approx.)         Delete "cyclohexasiloxan," and insert -- cyclohexasiloxane, --, therefor.
Line 22 (Approx.)         Delete "polydimethylsiloxan," and insert -- polydimethylsiloxane, --, therefor.
Line 23 (Approx.)         Delete "polydimethylsiloxan" and insert -- polydimethylsiloxane --, therefor.
Lines 29-30 (Approx.)     Delete "(3-propylene-methylsiloxan)-co-(dimethylsiloxan)" and insert -- (3-propylene-methylsiloxane)-co-(dimethylsiloxane) --, therefor.

Signed and Sealed this
Fourteenth Day of August, 2012

David J. Kappos
*Director of the United States Patent and Trademark Office*

Column 9
Lines 14-23 (Approx.)

Delete " 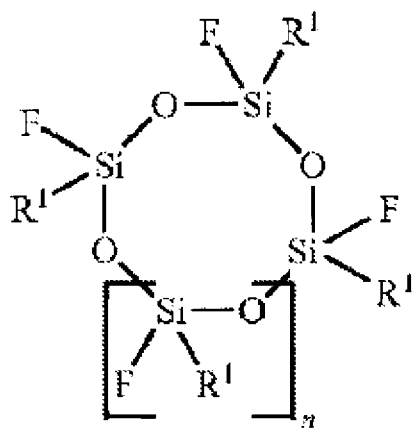 " and insert

-- 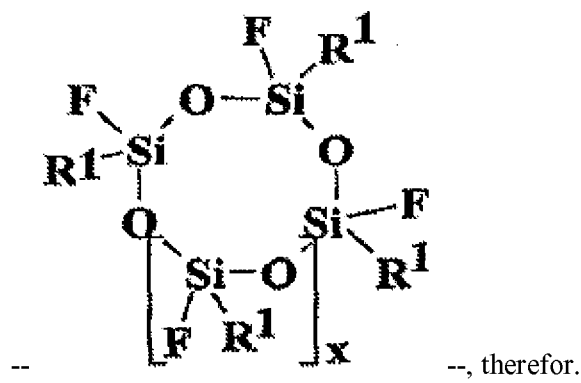 --, therefor.

Column 9
Line 32 (Approx.)   Delete "R$^{1}$" and insert -- R$^{2}$ --, therefor.
Line 32 (Approx.)   Delete "allylene" and insert -- alkylene --, therefor.

Column 10
Line 30   Delete "bisazolid" and insert -- bisazolide --, therefor.
Line 45   Delete "used" and insert -- use --, therefor.
Line 46   Delete "diimidazol" and insert -- diimidazole --, therefor.
Line 47   Delete "dibenzimidazol" and insert -- dibenzimidazole --, therefor.
Line 48   Delete "triazol" and insert -- triazole --, therefor.
Line 49   Delete "methylimidazol)" and insert -- methylimidazole) --, therefor.
Line 50   Delete "dibenzotriazol" and insert -- dibenzotriazole --, therefor.

Column 12
Line 25   Delete "compatibalizes" and insert -- compatibilizes --, therefor.
Line 27   Delete "compatibalizes" and insert -- compatibilizes --, therefor.

Column 13
Line 61   Delete "an" and insert -- on --, therefor.

CERTIFICATE OF CORRECTION (continued)
U.S. Pat. No. 8,124,714 B2

Column 16
Line 13      Delete "Quiva1ent:" and insert -- Quivalent: --, therefor.
Line 14      Delete "pm" and insert -- ppm --, therefor.
Lines 40-41     Delete (3-aminopropyl-methylsiloxan)-(dimenthylsiloxan)copolymer" and insert -- (3-aminopropyl-methylsiloxane)-(dimethylsiloxane)copolymer --, therefor.

Column 17
Line 38 (Approx.)   Delete "dibenzimidazol" and insert -- dibenzimidazole --, therefor.

Column 18
Line 14 (Approx.)   Delete "Viscosit<0.229" and insert -- Viscosity<0.229 --, therefor.

Column 22
Line 29 (Approx.)   In Claim 1, delete "$SiO_{4/2}$," and insert -- $SiO_{4/2}$; --, therefor.
Line 66 (Approx.)   In Claim 2, delete "is" and insert -- is a --, therefor.